(12) United States Patent
Minami

(10) Patent No.: US 10,966,849 B2
(45) Date of Patent: Apr. 6, 2021

(54) INDWELLING MEDICAL DEVICE HAVING BISTABLE STRUCTURE IN LUMEN ORGAN

(71) Applicant: Yamaguchi University, Yamaguchi (JP)

(72) Inventor: Kazuyuki Minami, Ube (JP)

(73) Assignee: YAMAGUCHI UNIVERSITY, Yamaguchi (JP)

( * ) Notice: Subject to any disclaimer, the term of this patent is extended or adjusted under 35 U.S.C. 154(b) by 39 days.

(21) Appl. No.: 16/491,949

(22) PCT Filed: Mar. 7, 2018

(86) PCT No.: PCT/JP2018/008867
§ 371 (c)(1),
(2) Date: Sep. 6, 2019

(87) PCT Pub. No.: WO2018/164205
PCT Pub. Date: Sep. 13, 2018

(65) Prior Publication Data
US 2020/0069446 A1 Mar. 5, 2020

(30) Foreign Application Priority Data
Mar. 8, 2017 (JP) .............................. JP2017-043453

(51) Int. Cl.
*A61F 2/915* (2013.01)

(52) U.S. Cl.
CPC .... *A61F 2/915* (2013.01); *A61F 2002/91541* (2013.01); *A61F 2002/91558* (2013.01); *A61F 2220/0091* (2013.01); *A61F 2250/001* (2013.01)

(58) Field of Classification Search
CPC ...... A61F 2/82; A61F 2/90; A61F 2/91; A61F 2/915
(Continued)

(56) References Cited

U.S. PATENT DOCUMENTS 9,005,265 B2 * 4/2015 Lootz ........................ A61F 2/91
623/1.11
10,271,976 B2 * 4/2019 Sirhan ........................ A61F 2/89
(Continued)

FOREIGN PATENT DOCUMENTS

JP 2002332791 A 11/2002
JP 2008507349 A 3/2008
(Continued)

OTHER PUBLICATIONS

ISA Japanese Patent Office, International Search Report Issued in Application No. PCT/JP2018/008867, dated Jun. 5, 2018, WIPO, 2 pages.
(Continued)

*Primary Examiner* — Suzette J Gherbi
(74) *Attorney, Agent, or Firm* — Alleman Hall Creasman & Tuttle LLP

(57) ABSTRACT

A cylindrical indwelling medical device is formed by connecting a plurality of struts in a circumferential direction of the device in such a way to share a rib in an axial direction in neighboring struts to form annular or spiral columns of struts and connecting the columns of struts in the axial direction via links. Each strut has at least one set of strut pieces providing a bistable structure for supporting a load from reducing a diameter of the indwelling medical device and portions for inducing snap-through buckling deformation. load is in a direction preventing reverse snap-through buckling deformation to hold an expanded diameter state of the device. After the indwelling medical device with its diameter reduced has been introduced into a luminal organ and has expanded its diameter to indwell there, the device can resist sufficiently against the reduction in diameter, thus maintaining the expanded diameter state of the device.

7 Claims, 4 Drawing Sheets

(58) Field of Classification Search
USPC .............................................. 623/1.15–1.48
See application file for complete search history.

(56) References Cited

U.S. PATENT DOCUMENTS

| | | | | |
|---|---|---|---|---|
| 2003/0069630 A1* | 4/2003 | Burgermeister | .......... | A61F 2/91 623/1.15 |
| 2006/0149357 A1* | 7/2006 | Shanley | .................... | A61F 2/91 623/1.16 |
| 2010/0249905 A1* | 9/2010 | Contiliano | ................ | A61F 2/91 623/1.16 |
| 2017/0128245 A1* | 5/2017 | Minami | .................... | A61F 2/93 |

FOREIGN PATENT DOCUMENTS

| | | | |
|---|---|---|---|
| JP | 2009160098 | A | 7/2009 |
| JP | 2009531135 | A | 9/2009 |
| JP | 2013135930 | A | 7/2013 |
| JP | 2014014698 | A | 1/2014 |
| JP | 2014508569 | A | 4/2014 |
| JP | 2014514111 | A | 6/2014 |
| JP | 5811580 | B2 | 11/2015 |
| JP | 2016064047 | A | 4/2016 |

OTHER PUBLICATIONS

ISA Japan Patent Office, Written Opinion Issued in Application No. PCT/JP2018/008867, dated Jun. 5, 2018, WIPO, 9 pages.

* cited by examiner

INDWELLING MEDICAL DEVICE HAVING BISTABLE STRUCTURE IN LUMEN ORGAN

TECHNICAL FIELD

The present invention relates to an indwelling medical device having a bistable structure for a luminal organ and particularly relates to an indwelling medical device having the bistable structure in which a state of the device with an expanded diameter can be held with bistable struts.

BACKGROUND OF THE INVENTION

A blood vessel is expanded with a balloon catheter to cause a stent to indwell therein for remedy of illnesses caused by vascular diseases such as myocardial infarctions or cerebral infarctions. While stents made of a metal material are commonly used as such stents, the stents made of a metal material remain permanently in a body. Accordingly, the stent made of a metal material cannot be applied to a young person whose body changes over time and it has a risk such that relapse of a blood vessel stricture is caused through mechanical stimulus for a long period of time. While the stent made of a metal material is superior in its strength, it is inferior in flexibility and is apt to impart mechanical stimulus or stress to an inner wall of a lumen such as a blood vessel and causes thickening of the inner wall of the lumen. In addition, diagnosis may become difficult because of a situation in which the metallic indwelling medical device remaining within the body affects an image by MRI (magnetic resonance imaging).

With an indwelling medical device made of a polymer material, stress to a wall of the lumen, which is a problem for the indwelling medical device made of a metal material, can be restrained. Such stress by a stent due to remaining permanently in a body can be solved by manufacturing the stent using a biodegradable/bioabsorbable polymer material, and an image by MRI is not affected by the stent. As such, a stent made of a polymer material is advantageous in solving defects of stents made of a metal material, and thus they have been frequently utilized in recent years.

On the other hand, the stents made of a polymer material has the possibility of reducing its diameter after having indwelt in a case of a stent expanded by a balloon, because it has lower elasticity and strength compared with one made of a metal material and easily creates creep deformation. Further, as a self-expanding stent, the stent made of a polymer material has inferior characteristics such that permanent deformation can be generated in a case where it is held in a reduced state for a long period of time or a reduction rate is made large, so that there is a possibility of losing a re-expanding property or a self-expanding ability.

A polymer stent, as an indwelling medical device for a luminal organ such as a blood vessel, is formed in a cylindrical shape and, after it has been inserted into the luminal organ in a reduced diameter state and then indwelt with the diameter expanded, acts so as to prevent a relapse of the luminal organ, and has a basic structure so arranged and formed that a network structure of cells consisting of struts and links is spread in circumferential and axial directions of a cylindrical shape.

Patent Document 1 discloses a stent providing wave-shaped spiral elements extending spirally around a longitudinal axis in which cells are formed by connecting the spiral elements neighboring in an axial direction with ribs extending between peak portions thereof. However, the stent is one made of a metal material and has inferior characteristics due to being made of the metal material.

Patent Document 2 discloses a pipe shaped stent in which a network structure of struts provides a plurality of circumferential wave-shaped rings and neighboring wave-shaped rings are connected between peak portions and bottom portions to form cells. With a stent having such a structure, an ability of resisting the action of reducing the diameter of the stent largely depends on the property of the material, and thus, there is a possibility that a stent with low rigidity as one made of the polymer material cannot resist well against the action in the diameter reduction direction of the stent and cannot maintain the function of a stent.

Patent Document 3 discloses a stent device in which strut elements formed to have peak portions and bottom portions arranged alternately is curled up circumferentially to form a stent, teeth are formed on a protruding portion formed on each of the peak portions of the strut elements, a plurality of peak portions with slits formed therein for inserting the protruding portions is formed in each of the bottom portions, the teeth formed on each of the peak portions allows the protruding portions in the peak portions to be inserted into the slits in the bottom portions and the strut elements forming a cylindrical stent have a configuration so as to resist a force in the diameter reduction direction of the stent. Further, Patent Document 4 discloses a stent made of a polymer material formed by connecting a plurality of T-shaped units, each of which consists of a head portion having a slit formed and a body portion having hook-shaped protrusions on one lateral side formed, arranged side by side, and curling up the arranged and connected T-shaped units and inserting each of the body portion into each of the head portions respectively, in which the body portion has an ability of changing width on a lateral side other than one where the hook-shaped protrusions are formed, and action by this ability of changing width allows the body portion to be inserted smoothly into the slit.

While an expanded stent state is held by a ratchet mechanism where pawls or hooks are engaged with slits in Patent Document 3 and Patent Document 4, these are stents made of a film material and have inferior characteristics such that flexibility for coping with bending cannot be obtained.

Patent Document 5 discloses a stent formed in a manner such that a series of cells combining thin struts and thick struts is rolled up spirally to form a cylindrical stent and the cells, each of which provides bistability, are connected by bridging elements. Further, Patent Document 6 discloses a stent made of a polymer material in which a plurality of cells combining strut pieces and links are arranged to form a network structure of a cylindrical stent made of the polymer material and the strut pieces connected to the links can be deformed by a pulling action of the links from one stable state to another stable state, thus providing bistability of the stent.

PRIOR ART DOCUMENTS

Patent Documents

Patent Document 1: JP Published Patent Application No. 2014-508569
Patent Document 2: JP Published Patent Application No. 2014-514111
Patent Document 3: JP Published Patent Application No. 2008-507349
Patent Document 4: JP Patent No. 5811580

Patent Document 5: JP Published Patent Application No. 2009-531135

Patent Document 6: JP Published Patent Application No. 2016-64047

DISCLOSURE OF THE INVENTION

Problems to be Resolved

A stent made of a polymer material such as Teflon (trade mark: polytetrafluoroethylene), polylactic acid, etc., has a high biocompatibility and a high flexibility as well as excellent followability to an organism compared with a stent made of a metal material, and the stent made of the polymer material is considered to be able to prevent an occurrence of restenosis or thrombus by a decrease or removal of stimulus to the organism. On the other hand, such a stent made of the polymer material has a low Young's modulus and does not have excellent plasticity near room temperature such as a stent made of a metal material has. Accordingly, a stent made of the polymer material employing a structure similar to one made of a metal material cannot secure a necessary force for expansion nor attain a sufficient remedial effect.

In Patent Document 5 or 6, it is disclosed that a holding ability against action in a diameter reduction direction of a stent is raised by providing bistable characteristics in the struts constituting the stent, and an appreciable force for expansion can be obtained with a stent disclosed in Patent Document 6. However, such a structure for sufficiently resisting pressure in the diameter reduction direction of the stent when it is raised is not provided in these documents, so that the possibility of reducing the diameter of the stent cannot be avoided.

It is a main object of the present invention to provide an indwelling medical device with high reliability that provides bistable characteristics of the struts constituting an indwelling medical device for use in a luminal organ such as a stent and has a structural property of being able to resist sufficiently against an action in a diameter reducing direction of the device even if it is raised.

Means for Solving the Problems

The present invention has been accomplished to solve the above object. The indwelling medical device for a luminal organ according to the present invention is such that a plurality of struts connected with each other are arranged to form a cylindrical shaped body having a network structure as a whole, wherein each strut is composed by connecting a plurality of strut pieces integrally via hinges and is deformed to be elongated in a circumferential direction of the indwelling medical device corresponding to expansion of a diameter of the device, each strut has at least one set of strut pieces having a bistable structure supporting a load acting to reduce the diameter of the device in a state where the set of strut pieces is deformed from one stable state through snap-through buckling deformation to another stable state in a process of elongation in the circumferential direction and the other strut pieces in the strut are connected so as to provide action to induce snap-through buckling deformation of the at least one set of the strut pieces having the bistable structure in the process of elongation of the strut in the circumferential direction, and the load acting to reduce the diameter of the device after the snap-through buckling deformation brings action preventing the at least one set of strut pieces having the bistable structure from creating snap-through buckling deformation in a reverse direction, so that a an expanded diameter state of the device is held.

The indwelling medical device for a luminal organ may be composed so that the at least one set of strut pieces having the bistable structure in each strut are two strut pieces connected via hinges to two neighboring ribs in the circumferential direction so as to be bridged over the two ribs, and a part including the other strut pieces providing action to induce the snap-through buckling deformation of the at least one set of the strut pieces is connected to the at least one set of strut pieces having the bistable structure or hinges connected thereto.

The indwelling medical device for a luminal organ may be composed so that the struts composing the indwelling medical device are arranged so that each two strut pieces neighboring in the circumferential direction of the indwelling medical device are connected with a rib shared therebetween to form an annular shaped body and a plurality of the annular shaped bodies are connected by connecting the ribs with each other via links in due positions in an axial direction to form the cylindrical indwelling medical device having the network structure, and the links have a thickness less than the ribs to be easily bent so that the indwelling medical device has flexibility as a whole.

The indwelling medical device for a luminal organ may be composed so that, in connecting the ribs with each other in due position between an annular shaped body of struts connected in the circumferential direction to another neighboring annular shaped body of struts connected in the circumferential direction, ribs neighboring in the axial direction are connected with each other via links for every more than one ribs in the circumferential direction and ribs disposed between the connected ribs in the circumferential direction are not connected with each other so that flexibility is provided in the indwelling medical device as a whole.

The indwelling medical device for a luminal organ may be composed so that the struts composing the indwelling medical device are arranged so that each two strut pieces neighboring in the circumferential direction of the indwelling medical device are connected with a rib shared therebetween to form a series of struts, the series of struts extends along a spiral line to form a cylindrical face and ribs succeeding forwards-backwards in an axial direction by one pitch are connected with each other via links in due positions so as to form the cylindrical indwelling medical device, and the links have a thickness less than the ribs to be easily bent so that the indwelling medical device has flexibility as a whole.

The indwelling medical device for a luminal organ may be composed so that, in connecting the ribs succeeding forwards-backwards in the axial direction by one pitch with each other via links in due positions to form the cylindrical indwelling medical device with series of struts extending along a spiral line in a cylindrical face, ribs neighboring in the axial direction are connected with each other via links for every more than one ribs in the circumferential direction and ribs disposed between the connected ribs in the circumferential direction are not connected with each other so that flexibility is provided in the indwelling medical device as a whole.

The indwelling medical device for a luminal organ may be composed so that that the part including the other strut pieces providing action to induce snap-through buckling deformation of the at least one set of the strut pieces having the bistable structure supporting the load acting in a diameter reduction direction of the indwelling medical device has a property of creating snap-through buckling deformation by itself along with inducing snap-through buckling deformation of the at least two strut pieces having the bistable structure when the indwelling medical device expands in diameter, so that each strut provide a double bistable structure.

Advantageous Effect of the Invention

With an indwelling medical device in a luminal organ according to the present invention, snap-through buckling deformation is created in at least one set of strut pieces providing a bistable structure in each of struts composing an indwelling medical device at a final step of action of expanding in diameter of the device to attain a stable state, and then, an action of causing the device to reduce in diameter imparts a load in a direction of preventing the creation of the snap-through buckling in a reverse direction to the at least one set of strut pieces providing the bistable structure, thus blocking the creation of the snap-through buckling in a reverse direction. With such a composition, an expanded diameter state of the device can be held, thereby allowing the indwelling medical device to securely hold the expanded diameter state as resisting sufficiently against the action of reducing the diameter of the device. Hence, a high reliability for an indwelling medical device is guaranteed.

BRIEF DESCRIPTION OF DRAWINGS

FIGS. 2(a) to 2(d) are views showing a configuration of a strut composing the indwelling medical device according to a first embodiment of the present invention, in which FIG. 2(a) shows a state with a diameter of the device reduced, FIG. 2(b) shows an intermediate state of the device expanding its diameter, FIG. 2(c) shows a state when the device is in a stage having further expanded its diameter and FIG. 2(d) shows a shape of the strut when the device has expanded its diameter to attain a stable state after snap-through buckling deformation respectively.

FIGS. 3(a) to 3(c) are views showing a configuration of a strut composing the indwelling medical device according to a second embodiment of the present invention, in which FIG. 3(a) shows a state with a diameter of the device reduced, FIG. 3(b) shows an intermediate state of the device expanding its diameter and FIG. 3(c) shows a shape of the strut when the device has expanded its diameter to attain a stable state after snap-through buckling deformation respectively.

FIG. 4 is a view showing a configuration of a strut according to a modified arrangement of the second embodiment in a state with the diameter of the device reduced.

FIGS. 5(a) to 5(c) are views showing a configuration of a strut composing the indwelling medical device according to a third embodiment of the present invention, in which FIG. 5(a) shows a state with a diameter of the device reduced, FIG. 5(b) shows an intermediate state of the device expanding its diameter and FIG. 5(c) shows a shape of the strut when the device has expanded its diameter to attain a stable state after snap-through buckling deformation.

DETAILED DESCRIPTION OF EMBODIMENTS

Figure 1A:
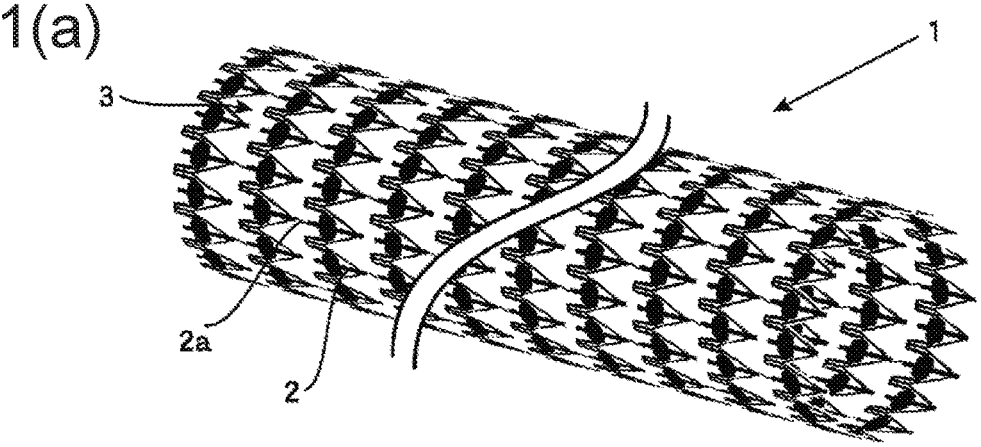
FIG. 1(a) is a schematic view showing an indwelling medical device in a luminal organ.

Embodiments of an indwelling medical device having a bistable structure for a luminal organ according to the present invention will be explained below. FIG. 1(a) is a schematic view showing an indwelling medical device. Here, an indwelling medical device 1 is composed by a material having elasticity so that a plurality of struts 3 having a bistable structure are arranged in a circumferential direction and in an axial direction of a cylindrical shape to form a network structure in the cylindrical shape. Respective two struts 3 neighboring with each other in a circumferential direction of the device are connected with a rib 2 in an axial direction shared by each other to form an annular shaped column of struts and the ribs 2 in the axial direction of a plurality of annular shaped column of struts are connected by links 2a with each other in due positions to form a cylindrical indwelling medical device 1. Here, the links 2a are thinner than the ribs 2 with a thickness to be bent more easily, so that the indwelling medical device 1 has flexibility as a whole.

Figure 1B:
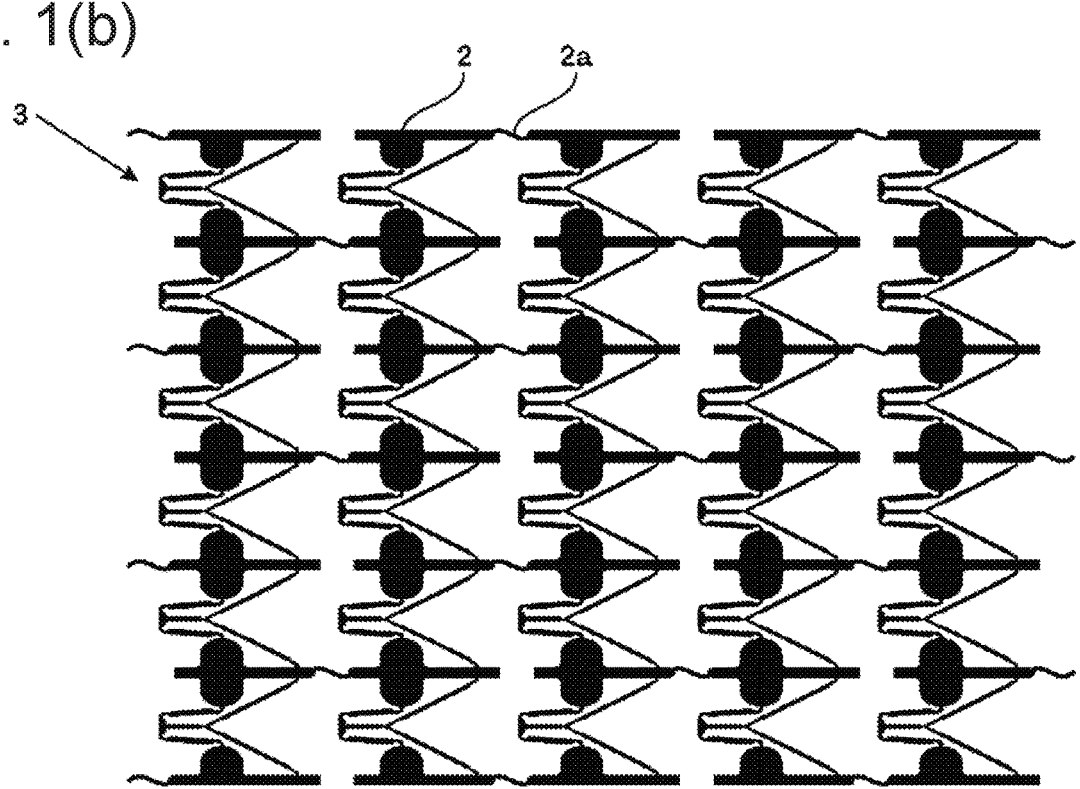
FIG. 1(b) is a partial enlarged view showing a part of the indwelling medical device in a cylindrical form to be spread.

FIG. 1(b) is a partial view showing a part of the cylindrical indwelling medical device to be expanded. Here, the struts 3 having a similar shape are arranged in a vertical direction as shown (circumferential direction of the device) and in a lateral direction as shown (axial direction of the device) and the ribs 2 arranged in the axial direction are connected with each other by the links 2a in due positions to form a network structure. As shown in FIG. 1(b), for example, every other rib 2 in the circumferential direction is connected with the ribs 2 arranged side by side in the axial direction by the links 2a between the right side of the column of the struts 3 disposed at leftmost position (in the first column of struts) and the neighboring column of the struts 3 (in the second column of struts). Further, between the second column of struts 3 and the next column to the right (third column of struts), the right side of the ribs 2 in the second column connected with ones in the first column are not connected with ones in the third column, but ribs 2 upward or downward by one in the circumferential direction are connected by the links 2a. In such a manner, every other rib 2 in the circumferential direction is connected with the ribs 2, 2 arranged side by side in the axial direction by the links 2a.

In a similar manner, every other rib 2 shared by the neighboring struts 3 in the circumferential direction is connected with each other by the links 2a and sites where ribs are not connected with each other are also of every other one. As shown in FIG. 1(b), the links 2a connecting the ribs 2, 2 with each other are positioned in a diagonal direction as seen for each strut 3, so that the struts 3 are connected with each other via the ribs 2 and the links 2a in a diagonal direction (spirally as seen on a cylindrical face).

While an arrangement of struts connected between the columns of the struts 3 in the circumferential direction is shown such that every other rib 2 is connected with the links 2a, an arrangement of struts connected between the columns of the struts 3 may be employed such that every third rib 2 is connected with the links 2a and further an arrangement of struts connected between the columns of the struts 3 is considered such that every fourth rib 2 is connected with the links 2a. Sites where the ribs 2 are connected by the links 2a with each other and sites where the ribs 2 are not connected with each other are distributed in a coexisting manner, so that the strength of a structure having flexibility is provided in a cylindrical indwelling medical device with the network structure of struts. Thus, it is defined in such respect which of the ribs 2 are to be connected by the links 2a.

A cylindrical body with the network structure is formed of a homogeneous polymer or metal material enabling elastic deformation to some extent and, as a cylindrical indwelling medical device having the network structure made of such material, has such thickness of the network structure that can sufficiently resist against pressure by a luminal inner wall where the device indwells and hold a configuration thereof. Further, in an indwelling medical device having the cylindrical network structure formed in such a manner that a plurality of struts 3 are connected in an annular shape with the rib 2 shared by neighboring struts and the ribs 2 are connected by the links 2a in the axial direction, each of the plurality of struts 3 connected in the circumferential direction with the ribs shared by neighboring struts can be deformed from a reduced state to an elongated state in the circumferential direction through bending-stretching deformation between the strut pieces composing the struts and connected by hinges, so that the diameter of the cylindrical shape of the device attains an expanded state. Additionally, each strut acts to prevent a change of the device such that the diameter of the cylindrical shape is reduced from an expanded state under an action of force from outside of the device and to hold the diameter of the cylindrical shape.

Such function of a strut as to allow an indwelling medical device to expand the diameter of the cylindrical shape and prevent the reduction of the diameter is based on characteristics such that each of a plurality of struts composing the cylindrical face of the device has bistability, with which a part of strut pieces composing each strut create the snap-through buckling deformation to be transferred from one stable state to another stable state during deformation of each strut towards diameter expansion of the device and, after having been transferred to the other stable state, prevents deforming towards an initial state, that is, towards diameter reduction of the device, thus enabling deformation in only one direction.

In order for each strut to possess such bistability, each strut is formed so as to have a structure with a particular configuration for creating snap-through deformation. Next, embodiments of specific structure with a particular configuration of a strut having such bistable structure will be explained below.

First Embodiment

Figure 2A:
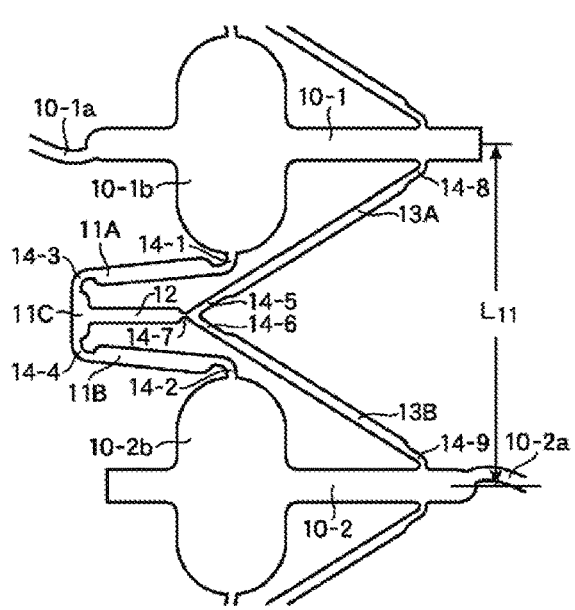
Figure 2B:
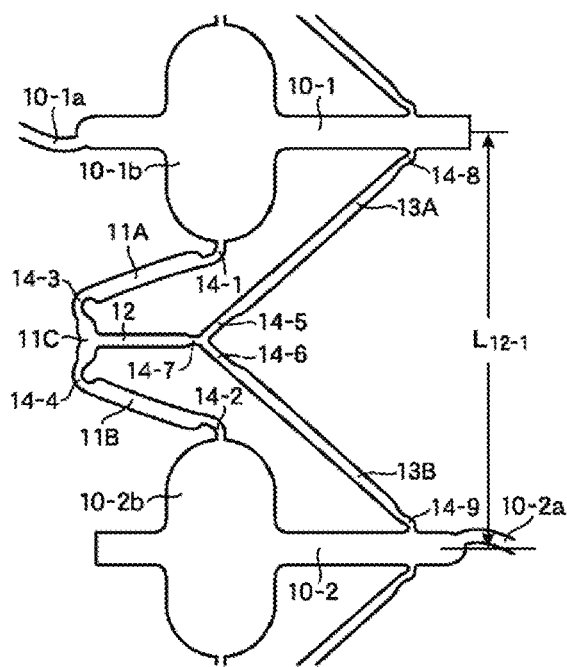
Figure 2C:
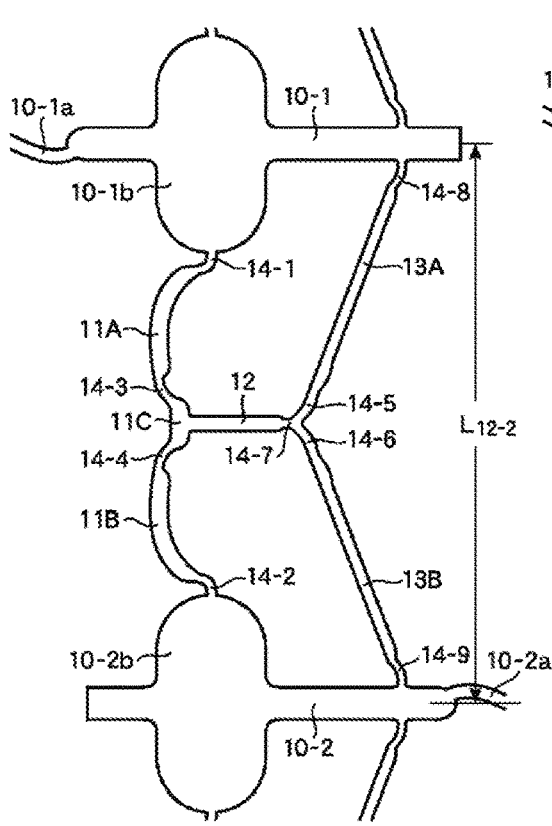
Figure 2D:
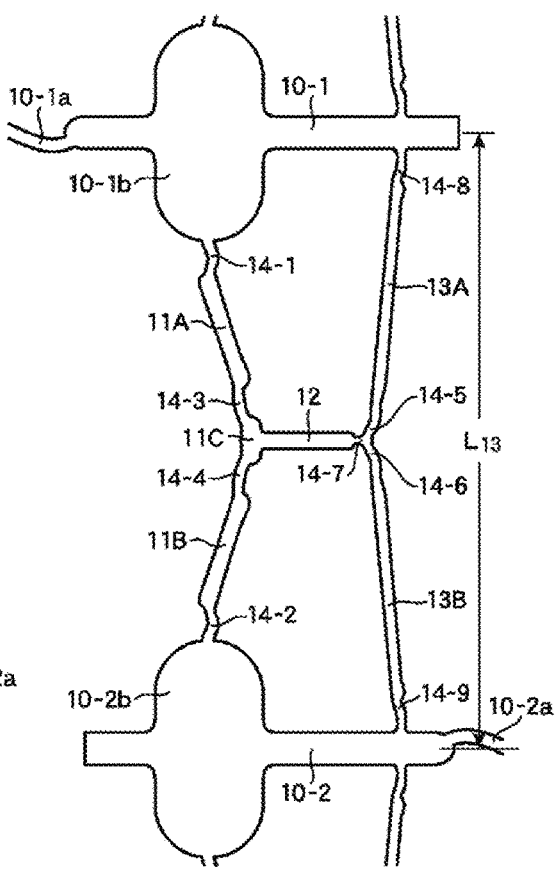

FIGS. 2(a) to (d) show a strut having bistable structure according to a first embodiment, in which FIG. 2(a) shows a shape of a strut in a state with diameter of an indwelling medical device reduced, FIG. 2(b) shows situation of the strut in an intermediate state of the device expanding its diameter, FIG. 2(c) shows a state when the device is in a stage having further expanded its diameter and FIG. 2(d) shows a shape of the strut when the device has expanded its diameter to attain a stable state after snap-through buckling deformation respectively. While FIGS. 2(a) to (d) show a strut, struts having a same shape as this are connected in the circumferential direction (vertical direction as shown) of the device with a rib in the axial direction shared by each other to form an annular shaped column of struts and ribs in the axial direction of a plurality of annular shaped column of struts are connected by links with each other in due positions. In such a manner, a cylindrical indwelling medical device having a network structure is formed by connecting annular shaped columns of struts in axial direction (lateral direction as shown).

In FIGS. 2(a) to (d), a left side of a substantially parallel upper side rib 10-1 is connected to a link 10-1a connected to a right side of a rib of a strut in a left position (not shown) and a right side of the rib 10-1 is not connected to a link. Further, a right side of a lower side rib 10-2 is connected to a link 10-2a for connection with a rib of a strut in a right position (not shown) and a left side of the rib 10-2 is not connected to a link.

Protruding portions 10-1b and 10-2b are formed integrally with the upper side rib 10-1 and lower side rib 10-2 on the confronting sides thereof respectively, so that a line through the centers of the protruding portions 10-1b and 10-2b is in a direction substantially vertical to the ribs 10-1 and 10-2. One ends of strut pieces 11A and 11B are connected integrally via hinges 14-1 and 14-2 to the protruding portions 10-1b and 10-2b respectively and the other ends of the strut pieces 11A and 11B are connected integrally via hinges 14-3 and 14-4 to one ends of a strut piece 11C respectively.

The strut piece 11C is connected integrally to an end of a strut piece 12 substantially vertical thereto to form a substantially T-shaped portion, the other end of the strut piece 12 is connected via hinges 14-7, 14-5, and 14-6 branching in two ways to one end of strut pieces 13A and 13B, respectively, the other end of the strut piece 13A is connected integrally via a hinge 14-8 to the rib 10-1, and the other end of the strut piece 13B is connected integrally via a hinge 14-9 to the rib 10-2, respectively.

The distance from the center position of the protruding portion 10-1b to the connecting position of the hinge 14-8 on the rib 10-1 is substantially equal to the distance from the center position of the protruding portion 10-2b to the connecting position of the hinge 14-9 on the rib 10-2, the length of the strut piece 11A is substantially equal to that of strut piece 11B and the length of the strut piece 13A is substantially equal to that of the strut piece 13B respectively. That is, the strut composed by these strut pieces has a substantially symmetrical shape for upper and lower parts as shown.

In such a manner, a strut is formed by connecting strut pieces integrally via a hinge or without a hinge, a plurality of struts are formed in the circumferential direction to form an annular shaped column of struts with a rib in the axial direction shared by each other, and further ribs are connected in the axial direction with each other by links in due positions between the annular shaped columns of struts, thus forming a cylindrical indwelling medical device having network structure. The device is formed using a polymer or a metal material enabling elastic deformation to a certain extent. Here, when homogeneous material is formed to be of a configuration as shown in FIGS. 2(a) to (d), easiness of deformation of each portion composing the configuration varies depending on thickness or length of a strut piece, hinge, etc., so that struts are formed to have bistability with consideration of difference in such easiness of deformation.

In the configuration of a strut shown in FIG. 2(a) in a reduced diameter state of an indwelling medical device, there are variations in thickness and ease of deformation of each portion. The protruding portion 10-1b has thickness such that substantially does not create bending deformation in relation to the rib 10-1 and the protruding portion 10-2b also has thickness similarly such that substantially does not create bending deformation in relation to the rib 10-2. The hinges 14-1, 14-2, 14-3, 14-4, 14-5, 14-6, 14-7, 14-8, and 14-9 are thinnest portions to be deformed most easily so as to undergo bending deformation superiorly when the indwelling medical device is deforming to expand its diameter.

The strut pieces 13A and 13B are thicker and more difficult to be in bending deformation than hinges 14-1 to 14-9 and the strut pieces 11A, 11B, and 11C are further thicker and more difficult to be in bending deformation. Whether bending deformation in such portions is created or not, and how bending deformation is created, depends not only on the thickness of the hinges and strut pieces, but depends also on the lengths thereof and additionally the relationship between disposition of the portions and deformation itself.

In order to cause the strut pieces 11A and 11B to create snap-through buckling deformation with movement in the axial direction of the strut piece 12 created by the deformation of the strut pieces 13A and 13B when the indwelling medical device is deformed to expand its diameter, it is necessary to make a stroke of movement by deformation of the strut pieces 13A and 13B sufficiently larger than that by deformation of the strut pieces 11A and 11B, so that the strut pieces 13A and 13B are made to be longer than the strut pieces 11A and 11B and, additionally, an opened angle between the strut pieces 13A and 13B is made larger than that between the strut pieces 11A and 11B in this embodiment.

This is due to a condition such that a larger opened angle between strut pieces causes a ratio of a stroke of movement in a lateral (axial) direction to one in a vertical (circumferential) direction to become larger, thus the protruding portions 10-1$b$ and 10-2$b$ are provided in order to satisfy such a relationship of these strut pieces and opened angles. Further, in connecting portions of the hinges 14-1 to 14-9 to strut pieces that are thicker than the hinges, etc., the connecting portions are made not to abruptly enlarge in thickness but to gradually enlarge in thickness so that a concentration of stress in these portions may not be so high during bending deformation.

A situation, in which a strut formed by connecting integrally ribs, strut pieces, and hinges in such a manner is deformed according to deformation of an indwelling medical device to expand diameter, will be explained. FIG. 2($a$) shows a state of the strut when the indwelling medical device is reduced with its diameter being smallest and a distance between the centers of the rib 10-1 and 10-2 is $L_{11}$. The strut pieces 11A and 11B are substantially straight and in a closed state with a small angle to an axial direction of the device. The strut pieces 13A and 13B are also substantially straight and have a smallest angle to an axial direction of the device.

With the action of the device expanding its diameter, distance between the ribs 10-1 and 10-2 is increased from the above state to enlarge angle formed between the strut pieces 13A and 13B. Corresponding to this, the strut is deformed in such a manner that the ends of the strut pieces 11A and 11B connected via the T-shaped strut pieces 12, 11C and hinges 14-3 and 13-4 to the strut pieces 13A and 13B are pulled to move rightwards as shown. This deformation is mainly due to bending deformation of the hinges.

A state shown in FIG. 2($b$) is attained with action of the device expanding its diameter in which distance between the ribs 10-1 and 10-2 is $L_{12\text{-}1}$. The strut pieces 11A and 11B remain in a substantially straight state to have an opened angle between them. Then, the strut pieces 13A and 13B also have an opened angle that widens and is larger than that between the strut pieces 11A and 11B, which is due to a relationship of the length of the strut pieces and positions of the connection thereof.

When the distance between the ribs 10-1 and 10-2 is increased from the above state to be $L_{12\text{-}2}$ so that the diameter of the device attains near to its maximum, the strut is in a state as shown in FIG. 2($c$). In a process of being transferred to the latter state, when distance between the ribs 10-1 and 10-2 is increased, an angle formed by the strut pieces 11A and 11B, each of which is in a state of straight line, is increased and at the same time an angle formed by the strut pieces 13A and 13B is increased respectively to cause the hinges 14-5 and 14-6 to move rightwards as shown, according to a relationship of length in the strut pieces 11A, 11B and the strut pieces 13A, 13B and angles formed by these. In this, a stroke of movement of the hinges 14-5 and 14-6 inherently tends to be larger than a rightward stroke of movement of the strut piece 11C with opening of the strut pieces 11A and 11B. Due to this, with ends of the strut pieces 11A and 11B being pulled rightwards via the strut piece 12, strut piece 11C, hinges 14-3 and 14-4, the strut pieces 11A and 11B cannot hold a substantially straight shape anymore to become bent by being pulled rightwards because of positional relationship between the strut piece 11C and the hinge 14-1 and between the strut piece 11C and the hinge 12-2 at this time, and this state exhibits the strut pieces 11A and 11B being transferred already to a stage of snap-through buckling deformation.

When distance between the ribs 10-1 and 10-2 is expanded to attain one of $L_{13}$ where snap-through buckling deformation occurs, snap-through buckling deformation is induced by a force pulling ends of the strut pieces 11A and 11B to the side of the strut piece 11C rightwards, so that the strut piece 11C moves beyond a position on a straight line connecting the hinges 14-1 and 14-2 to attain the position shown in FIG. 2($d$). In this state, the strut pieces 11A and 11B return to a straight shape and are stable in a situation with an angle over 180°.

In such a manner, FIG. 2($b$) shows that the strut pieces 11A and 11B are in one stable state of bistability before snap-through buckling deformation and FIG. 2($d$) shows that the strut pieces 11A and 11B, going through a state shown in FIG. 2($c$) just before snap-through buckling deformation, are transferred to the other stable state of bistability. Here, the snap-through buckling deformation is created as a motion in an extremely short time.

For the strut pieces 11A and 11B and the hinges 14-1, 14-2, 14-3, and 14-4 connected with them, the initial shape shown in FIG. 2($a$) is in a state before deformation. Then, going through a state shown in FIG. 2($b$) and a state shown in FIG. 2($c$) while portions of the hinges connecting the strut pieces 11A and 11B between the ribs 10-1 and 10-2 are deformed elastically according to deformation of each strut corresponding to expanded diameter of the indwelling medical device, the strut pieces 11A and 11B and the hinges 14-1, 14-2, 14-3, and 14-4 connected with them come to a state shown in FIG. 2($d$). This state is such that, elastic deformation is raised to a high level with a high restoring force through a process to this state and the restoring force is raised, as a resisting force to elongation of the strut with bending deformation of the strut pieces, creates a high resisting force to deformation of further expanding diameter of the device. Consequently, even if a distance between the ribs 10-1 and 10-2 is to be further expanded with a force acing to expand diameter of the device, the strut pieces 11A and 11B cannot be deformed to raise a level of bending further from the state shown in FIG. 2($d$) where the strut pieces have attained the other stable state.

Further, an action of pressing the strut pieces 11A and 11B from the side of the protruding portions 10-1$b$ and 10-2$b$ with the ribs 10-1 and 10-2 narrowing the distance therebetween results in preventing the strut pieces 11A and 11B having attained the state shown in FIG. 2($d$) from returning with a restoring force. Even if the strut pieces 13A and 13B in right side as shown are to reduce an angle between them, action of pushing back the strut pieces 11A and 11B leftwards does not occur, because the former strut pieces are thinner than the latter and more easily bent.

In such a manner, while the strut having the configuration shown in FIGS. 2(a) to (d) is arranged so that specifically snap-through buckling deformation occurs in the strut pieces 11A and 11B, the strut pieces 13A and 13B compose portions for inducing snap-through buckling deformation in the strut pieces 11A and 11B via the T-shaped portion of strut pieces 11C and 12. After each strut, from a state shown in FIG. 2(a) with diameter of the indwelling medical device reduced, has attained a state shown in FIG. 2(d) with diameter of the device expanded as the other stable state of bistability of the strut, action of reducing diameter of the device, even if it were applied, is blocked by bistability of each strut with accumulated elastic force.

In order to create snap-through buckling deformation in the strut pieces 11A and 11B from a state shown in FIG. 2(a) to a state shown in FIG. 2(d), it becomes a condition for this to establish a situation such that, when the ribs 10-1 and 10-2 are to expand a distance therebetween from a state shown in FIG. 2(a), the strut pieces 13A and 13B open an angle therebetween, causing the strut piece 11C to move rightwards, faster than the strut pieces 11A and 11B open the angle therebetween, causing the strut piece 11C to move rightwards, thus pulling the strut piece 11C rightwards. Hence, it is necessary to decide elements of configuration of the struts such as height of the protruding portions 10-1b and 10-2b, length of strut pieces 11A and 11B as well as strut pieces 13A and 13B and opened angles between these strut pieces, and a position of connecting to the rib 10-1 and 10-2 via hinges so as to satisfy this condition.

An indwelling medical device with each strut in a state shown in FIG. 2(a) is mounted on a balloon catheter in a thin state, which is inserted into a desired luminal organ. Then, the diameter of the indwelling medical device is expanded by expanding the balloon catheter, after which it is caused to indwell within the luminal organ. In this manner, the indwelling medical device within the luminal organ can secure a function of holding its configuration, resisting against pressure from the inner wall of the luminal organ.

When action from outside is applied to a diameter reduction direction of the indwelling medical device after the device has attained the expanded diameter state, for the indwelling medical device provided with the struts having the configuration shown in FIGS. 2(a) to (d), the action result in being applied to a direction so as not to reverse the strut to an initial shape, that is, to advance deformation after snap-through buckling deformation, so that the action is blocked by the elastic force accumulated in the strut pieces having undergone the snap-through buckling deformation. After all, it is possible for the struts to hold the indwelling medical device in a stable manner to be in the expanded diameter state.

Here, the indwelling medical device is formed as a whole through processing a homogeneous polymer or metal material enabling elastic deformability to a certain extent, in which a plurality of struts composed to have strut pieces connected by hinges, etc., respectively is arranged so as to form the network structure in a cylindrical shape. In this, strut pieces, hinges, ribs, links, etc., as portions composing the struts are formed to have a thickness and length for providing easiness of bending deformation of portions such as strut pieces and hinges composing the struts adapted to deformation of shape of each strut corresponding to an action causing the device to be deformed when it is applied to the device. This is similar in the embodiments explained below.

Second Embodiment

Figure 3A:
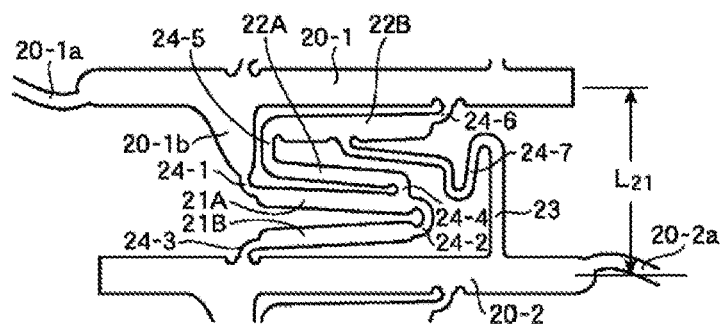
Figure 3B:
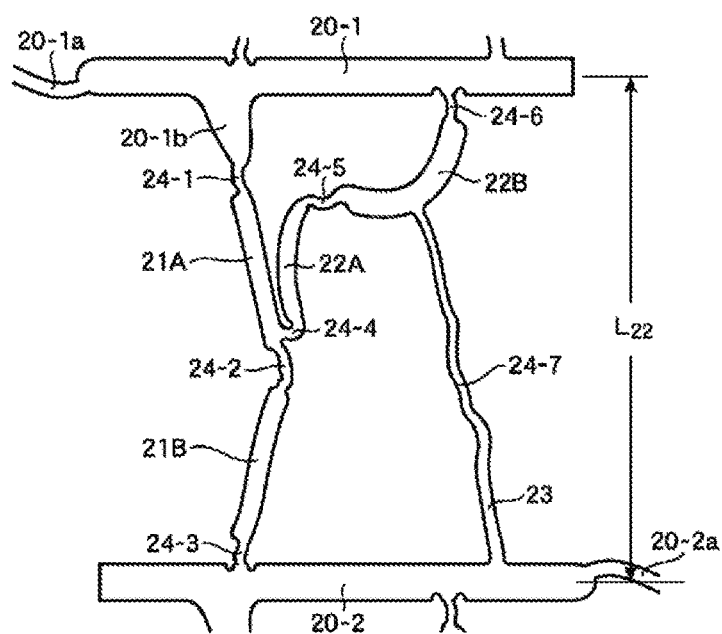
Figure 3C:
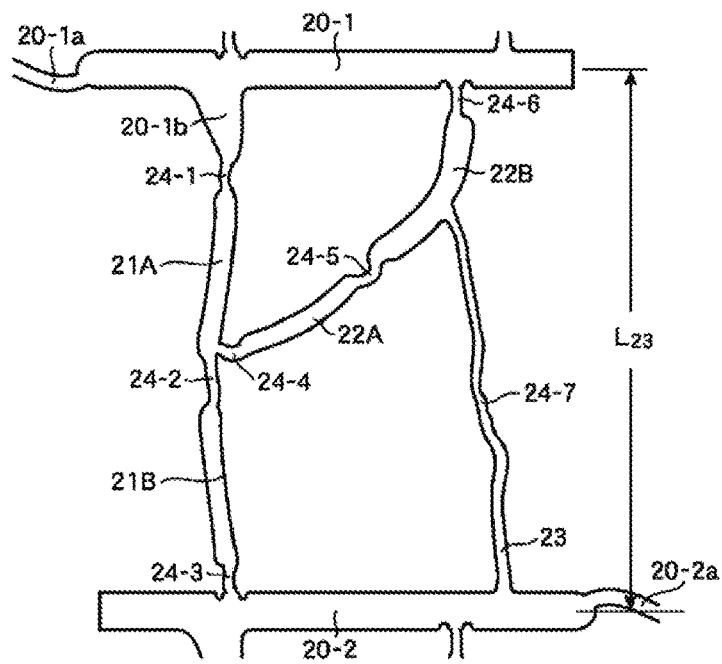

FIGS. 3(a) to (c) show a strut having bistable structure according to a second embodiment, in which FIG. 3(a) shows a shape of a strut in a state with diameter of an indwelling medical device reduced, FIG. 3(b) shows situation of the strut in an intermediate state of the device expanding its diameter and FIG. 3(c) shows a situation of the strut when the device has expanded its diameter to attain a stable state after snap-through buckling deformation of the device respectively. While FIGS. 3(a) to (c) show a stent, struts having a same shape as this are connected in the circumferential direction of the device with a rib in the axial direction shared by each other to form an annular shaped column of struts and the plurality of annular shaped columns of struts are connected by links with each other in due positions to form a cylindrical indwelling medical device having network structure as a whole.

In FIGS. 3(a) to (c), a left side of a substantially parallel upper side rib 20-1 is connected to a link 20-1a connecting this to a right side of a rib of a strut in a left position (not shown) and a right side of the rib 20-1 is not connected to a link. Further, a right side of a lower side rib 20-2 is connected to a link 20-2a for connection with a rib of a strut in a right position (not shown) and a left side of the rib 20-2 is not connected to a link.

In the configuration of the strut shown in FIGS. 3(a) to (c), a protruding portion 20-1b is provided integrally on the underside of the upper side rib 20-1 and one end of a strut piece 21A is connected to the protruding portion 20-1b via a hinge 24-1. One end of a strut piece 21B is connected to the upper side of the confronting rib 20-2 via a hinge 24-3 and the other ends of the strut pieces 21A and 21B are connected with each other via hinge 24-2.

A hinge 24-4 is connected to the other end of the strut piece 21A in a manner branching from the hinge 24-2 connected thereto and one end of a strut piece 22A is connected to the other end of the strut piece 21A via the hinge 24-4. One end of a strut piece 22B is connected to the other end of the strut piece 22A via a hinge 24-5 and the other end of the strut piece 22B is connected to the underside of the rib 20-1 via a hinge 24-6.

One end of another strut piece 23 is connected via a hinge 24-7 to the strut piece 22B in an intermediate position thereof and the other end of the strut piece 23 is connected directly to the rib 20-2. The hinge 24-7 is longer than other hinges and its end other than one connected to the strut piece 23 is connected to the strut piece 22B in the intermediate position thereof to form a smoothly bent shape in a state shown in FIG. 3(a). Further, a straight line connecting a position where the hinge 24-1 is connected to the top of the protruding portion 20-1b and a position where the hinge 24-3 is connected to the rib 20-2 is in a substantially vertical direction.

It is similar to the case of the first embodiment in that a plurality of struts, each of which is formed by connecting strut pieces integrally with or without a hinge, are connected in the circumferential direction to form an annular shaped column of struts with a rib in the axial direction shared by each other, such annular shaped columns of struts are connected in the axial direction with each other by links in due positions in the axial direction to form a cylindrical indwelling medical device having the network structure as a whole. The device is formed using a polymer or a metal material enabling elastic deformation to a certain extent and the struts are formed to have bistability with consideration of the difference in ease of deformation of each portion composing the configuration that varies depending on thickness or length of a strut piece, hinge, etc.

In a composition of a strut shown in FIGS. 3(a) to (c), the protruding portion 20-1b has a thickness such that it substantially does not create bending deformation in relation to the rib 20-1 and the hinges 24-1, 24-2, 24-3, 24-4, 24-5, 24-6, and 24-7 are the thinnest portions deformed most easily so as to undergo bending deformation superiorly when the indwelling medical device is in deformation to expand its diameter. The strut pieces 21A, 21B, 22A, and 22B have a thickness to a certain extent, being thicker and having a lower degree in ease of bending deformation than the hinges 24-1 to 24-7.

It is similar to the case of the first embodiment in that whether bending deformation in portions is created or not, and how bending deformation is created, depends not only on the thickness of the hinges and strut pieces, but depends also on the length thereof and the relationship between the disposition of the portions and deformation itself. In addition, in connecting portions of the hinges 24-1 to 24-7 to strut pieces, etc., thicker than the hinges, the connecting portions are made not to abruptly enlarge in thickness but to gradually enlarge in thickness so that the concentration of stress in these portions may not be so high during bending deformation.

A situation, in which the strut having the above explained composition is deformed according to the deformation of the indwelling medical device to expand its diameter will be explained. FIG. 3(a) shows a state of the strut when the indwelling medical device is reduced with its diameter being smallest and a distance between the centers of the ribs 20-1 and 20-2 is $L_{21}$. The strut pieces 21A and 21B are substantially straight and in a bent situation rightwards with a small angle via the hinge 24-2 between the protruding portion 20-1b and the rib 20-2, and also the strut pieces 22A and 22B are substantially straight and in a bent situation leftwards via the hinge 24-5 between the hinge 24-4 connected to the end of the strut piece 21A and the hinge 24-6 connected to the rib 20-1.

With action of the device expanding its diameter from this state, the distance between the ribs 20-1 and 20-2 is increased to be $L_{22}$ with the diameter of the device expanded near to maximum in a state as shown in FIG. 3(b). While an angle formed by the strut pieces 21A and 21B is large at this time, it is smaller than 180° and the strut pieces are in a state before the snap-through deformation with a nearly straight shape. While the angle formed by the strut pieces 22A and 22B also becomes large, the hinge 24-7 with one end connected to the strut piece 22B in the intermediate position, being pulled by the strut piece 22B, changes its state from a bent one to a substantially straight one, so that the strut piece 22B attains a state to be bent in a little downwards convex shape pulled by the strut piece 23.

In a step in which the strut pieces 21A and 21B attains the state shown in FIG. 3(b), a length of the strut pieces 22A and 22B connected via hinges in a substantially straight row is more than a distance between the hinges 24-4 and 24-6. Due to this, while the hinge 24-4 is pushed leftwards at first during a step of enlarging an angle formed by the strut pieces 22A and 24B, strut pieces 22A and 22B cannot hold a substantially straight shape, because resistance to deformation in the strut pieces 21A and 21B restricts leftward movement of the hinge 24-4, so that the strut piece 22B is in a state pulled to the side of the strut piece 23 to be bent in a little downwards convex shape and the strut piece 22A is bent in a little upwards convex shape.

The indwelling medical device expands its diameter further from the state shown in FIG. 3(b) to a state shown in FIG. 3(c) so that distance between the ribs 20-1 and 20-2 is somewhat larger than $L_{22}$ and becomes $L_{23}$. In this process, the strut piece 22B is further pulled by the hinge 24-7 to cause the hinge 24-5 to move right-downwards from the state shown in FIG. 3(b). As the strut piece 22A connected thereto via the hinge 24-5 is also pulled with this motion, the strut pieces 22A and 22B move leftwards so as to be side by side in substantially straight shape. However, because the leftward movement stroke of the strut pieces 21A and 21B in an opening process of an angle formed between them is smaller than movement stroke of the hinge 24-4, the difference is absorbed by the strut piece 22A transferred to be in a bent state. Consequently, these sides are in a situation of pushing each other via the hinge 24-4.

Under such a situation, as the portion of the hinge 24-5 between the strut pieces 22A and 22B continue action of moving right-downwards, the strut piece 22A is transferred to be bent in a reversed shape as shown in FIG. 3(c) at a certain moment. This deformation occurs in an instant moment as snap-through buckling deformation. In this deformation, the strut piece 22A presses ends of the strut pieces 21A and 21B abruptly via the hinge 24-4. As a consequence, the strut pieces 21A and 21B connected via the hinge 24-2, are deformed so as to move leftwards as shown in an instant moment, that is, deformed such that the a state of strut pieces 21A and 21B with an angle between them smaller than 180° goes abruptly beyond the position corresponding to a straight line to a state with an angle larger than 180°. This is by snap-through buckling deformation.

In the process of attaining a state shown in FIG. 3(c), extent of elastic bending deformation is raised in the hinges 24-2 connecting the strut pieces 21A and 21B to increase restoring force, which presents a state of providing a high resisting force to deformation to expand diameter of the device with bending deformation of the strut pieces providing a force resisting to deformation of elongation. Consequently, even if distance between the ribs 20-1 and 20-2 is to be expanded further when a force to expand diameter of the device is applied, this state does not allow further deformation. Therefore, even if distance between the ribs 20-1 and 20-2 is to be expanded further when a force to expand diameter of the device is applied, the strut pieces 21A and 21B cannot be deformed so as to raise extent of bending deformation further from a state shown in FIG. 3(c) where stable state has been attained after snap-through buckling deformation. Further, action by the ribs 20-1 and 20-2 pressing the strut pieces 21A and 21B from both sides so as to reduce distance between the ribs is one preventing the strut pieces 21A and 21B having attained the state shown in FIG. 3(c) from returning the initial state by restoring force.

Further, when the strut pieces 21A and 21B are to raise extent of their bending movement with action of the ribs 20-1 and 20-2 to reduce distance between them, the strut pieces 22A and 22B are in a state of being aligned in a straight line and enabled to hold tensile force, so that the tensile force prevents the hinge 24-2 from moving further leftwards, thus preventing the ribs 20-1 and 20-2 from moving to reduce the distance between them.

Furthermore, in such a situation, the rib 20-1, the strut piece 22B, 22A, 21A, the protruding portion 20-1b, and the hinges connecting these form a substantially triangular shape. As the triangular shape is superior in stability of shape, thus providing resistivity to deformation against an external force in a direction perpendicular to one such that the ribs 20-1 and 20-2 reduce the distance between them, so that the stability of the shape superior to the first embodiment can be realized. Still furthermore, also the strut pieces 22A and 22B inducing snap-through buckling deformation of the strut pieces 21A and 21B undergo snap-through buckling deformation, so that security is raised by such double bistable structure.

In such a manner, in a strut having the configuration shown in FIGS. 3(*a*) to (*c*), the strut pieces 21A and 21B specifically undergo snap-through buckling deformation and the strut pieces 22A and 22B are portions for inducing snap-through deformation in the strut pieces 21A and 21B. Starting from an initial state shown in FIG. 3(*a*) such that each strut corresponds to a state where the diameter of the indwelling medical device is reduced, each strut attains a state shown in FIG. 3(*b*) such that each strut corresponds to a state where the diameter of the device is expanded, and then still further attains a state shown in FIG. 3(*c*) as the other stable state of the bistability of the strut pieces, after which action on the device towards the diameter reduction direction of the device is blocked even if it were applied.

In order to create snap-through buckling deformation in the strut pieces 21A and 21B from a state shown in FIG. 3(*b*) to a state shown in FIG. 3(*c*), it becomes necessary that, when the ribs 20-1 and 20-2 expand distance between them with angle formed by the strut pieces 21A and 21B opened up to a state shown in FIG. 3(*b*), distance between the hinges 24-4 and 24-6 as connecting positions of the strut piece 21A or the rib 20-1 with the strut pieces 22A or 22B respectively is less than a length of the strut pieces 22A and 22B in a serial elongated state, due to which the strut pieces 22A and 22B are forced to be in a bent state as shown in FIG. 3(*b*). Further, it is necessary for satisfying this condition to decide elements of configuration of the struts such as the height of the protruding portion 20-1*b*, the length of strut pieces 21A and 21B as well as strut pieces 22A and 22B, the length of the hinges 24-7, the length of the strut piece 23 and the positions in connection to the rib 20-2.

The indwelling medical device with each strut in a state shown in FIG. 3(*a*) is mounted on a balloon catheter in a thin state, which is inserted into a desired luminal organ. Then, diameter of the indwelling medical device is expanded by expanding the balloon catheter, after which it is caused to indwell within the luminal organ. With this, the indwelling medical device within the luminal organ can secure a function of holding its configuration resisting to pressure from the inner wall of the luminal organ.

When the action from outside is applied to the diameter reduction direction of the indwelling medical device after the device has attained a state with the diameter expanded, for the indwelling medical device provided with struts having the configuration shown in FIGS. 3(*a*) to (*c*), the action result in being applied to a direction so as not to reverse the strut to an initial shape, that is, to advance the deformation after snap-through buckling deformation, so that the action is blocked by the elastic force accumulated in the strut pieces having undergone snap-through buckling deformation. Therefore, it is possible for the struts to hold the indwelling medical device in a stable manner to be in a state with its diameter expanded.

FIG. 4 is a view showing a configuration of a strut according to a modified arrangement of the second embodiment in a state with the diameter of the device reduced. While this configuration is basically similar to one shown in FIG. 3(*a*), the configuration of the strut shown in FIG. 4 differs from one shown in FIG. 3(*a*) in that the strut piece 23 is connected to the strut piece 22A on a side near to the hinge 24-5 (left side as shown) and otherwise similar to one shown in FIG. 3(*a*).

It is similar to the case as shown in FIGS. 3(*a*) to (*c*) in that, when each strut is elongated as the indwelling medical device expands its diameter, the strut piece 22A is pulled to the side of the strut piece 23 via the hinge 24-7, causes snap-through buckling deformation to occur, is transferred to be bent in a reversed shape and abruptly presses a portion where the strut pieces 21A and 21B are connected via the hinge 24-4 to create snap-through buckling deformation in the strut pieces 21A and 21B.

Third Embodiment

FIGS. 5(*a*) to (*c*) show a strut having the bistable structure according to a third embodiment, in which FIG. 5(*a*) shows a shape of a strut in a state with diameter of the indwelling medical device reduced, FIG. 5(*b*) shows a situation of the strut in an intermediate state of the device expanding its diameter, and FIG. 5(*c*) shows situation of the strut when the device has expanded its diameter to attain a stable state after snap-through buckling deformation of the device respectively. While FIGS. 5(*a*) to (*c*) show a stent, struts having the same shape as this are connected in the circumferential direction of the device with a rib in the axial direction shared by each other to form an annular shaped column of struts and the plurality of annular shaped columns of struts are connected by links with each other in due positions to form a cylindrical indwelling medical device having the network structure as a whole.

In FIGS. 5(*a*) to (*c*), a left side of a substantially parallel upper side rib 30-1 is connected to a link 30-1*a* connecting this to a right side of a rib of a strut in a left position (not shown) and a right side of the rib 30-1 is not connected to a link. Further, a right side of a lower side rib 30-2 is connected to a link 30-2*a* for connection with a rib of a strut in a right position (not shown) and a left side of the rib 30-2 is not connected to a link.

In the configuration of the strut shown in FIGS. 5(*a*) to (*c*), one end of a strut piece 31A is connected via a hinge 36-1 to underside of the upper side rib 30-1, one end of a strut piece 31B is connected via a hinge 36-3 to the upper side of the confronting rib 30-2, the other ends of the strut pieces 31A and 31B are connected with each other via a hinge 36-2. The hinge 36-2 has a protruding portion in an intermediate position to be connected to another portion.

In a right side position of the strut pieces 31A and 31B as shown, one end of a strut piece 32A is connected via a hinge 36-4 to underside of the upper side rib 30-1, one end of a strut piece 32B is connected via a hinge 36-6 to the upper side of the rib 30-2, the other ends of the strut pieces 32A and 32B are connected with each other via a hinge 36-5. The hinge 36-5 has a protruding portion in an intermediate position to be connected to another portion.

In FIG. 5(*a*), a straight line connecting positions where the strut pieces 31A and 31B are connected to the rib 30-1 or 30-2 via the hinge 36-1 or 36-3, respectively, is substantially in a direction perpendicular to the ribs 30-1 and 30-2. Further, a straight line connecting positions where the strut pieces 32A and 32B are connected to the rib 30-1 or 30-2 via the hinge 36-4 or 36-6 respectively is substantially in a direction perpendicular to the ribs 30-1 and 30-2, and the strut pieces 31A, 31B, 32A, and 32B are of an equivalent length. In such a manner, the strut pieces 31A and 31B are arranged so as to form a shape of ">" and the strut pieces 32A and 32B are arranged so as to form a shape of "<", as an arrangement forming, as an arrangement substantially symmetrical in respect to a center vertical line and also substantially symmetrical with respect to a center lateral line.

End side of branch strut pieces 33A and 33B composing a substantially U-shaped thick strut piece 33 is connected to the protruding portion in the intermediate position of the hinge 36-2 connecting the strut pieces 31A and 31B, one end of a strut piece 34A is connected via a hinge 36-7 to an end of the branch strut piece 33A and the other end of the strut piece 34A is connected to one end of a hinge 36-8 having a protruding portion in an intermediate position. Further, one end of the strut piece 34B is connected via a hinge 36-9 to an end of the branch strut piece 33B and the other end of the strut piece 34B is connected to the other end of the hinge 36-8. One end of a strut piece 35 is connected to the protruding portion in the intermediate position of the hinge 36-8 and the other end of the strut piece 35 is connected to a protruding portion in an intermediate position of the hinge 36-5, via which the strut piece 35 is connected to the strut pieces 32A and 32B.

The branch strut pieces 33A and 33B of the strut piece 33 are equivalent and the strut pieces 34A and 34B have an equivalent length so that configuration formed by these portions is symmetric in respect to a center lateral line. While the strut piece 33 including the branch strut pieces 33A and 33B, being especially thick, are not deformed by so large amount but undergo bending deformation to some extent during action of the indwelling medical device expanding its diameter, the strut pieces 31A and 31B as well as strut pieces 32A and 32B undergo snap-through buckling deformation to support the ribs 30-1 and 30-2 resisting to action reducing distance between them. Further, the strut pieces 34A and 34B undergo snap-through buckling deformation under a pulling action thereto to be in reversed shape, and the strut piece 35, as a portion for transferring pulling-pressing action at this time, has a thickness less than the substantially U-shaped strut piece 33.

It is similar to the case of the first embodiment in that a plurality of struts, each of which is formed by connecting strut pieces integrally via a hinge or without hinge, is connected in the circumferential direction to form an annular shaped column of struts with a rib in the axial direction shared by each other, such annular shaped columns of struts are connected in the axial direction with each other by links in due positions in axial direction to form the cylindrical indwelling medical device having network structure as a whole, the device is formed using the polymer or metal material enabling elastic deformation to certain extent and the struts are formed to have bistability with consideration of difference in easiness of deformation of each of portions composing the configuration that varies depending on the thickness or the length of a strut piece, hinge, etc.

Figure 5A:
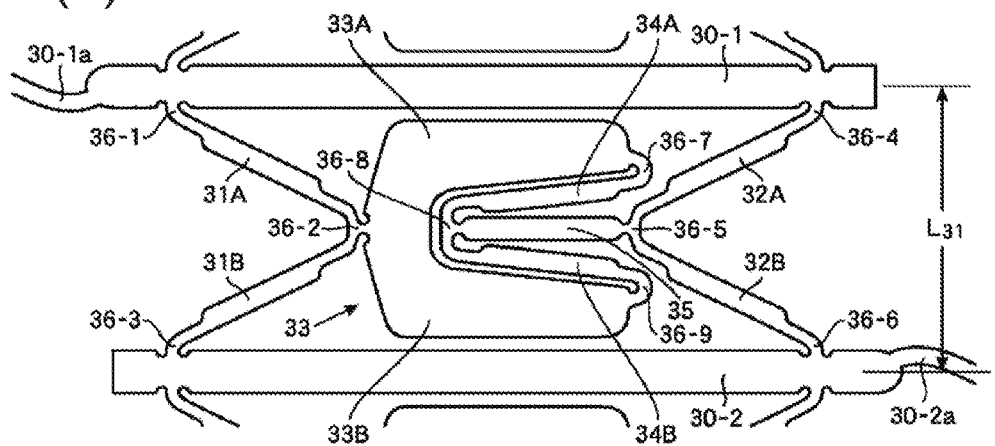

A situation, in which the strut having the above explained composition is deformed according to deformation of an indwelling medical device to expand its diameter will be explained. FIG. 5(a) shows a state of the strut when the indwelling medical device is reduced with its diameter being smallest and distance between the centers of the ribs 30-1 and 30-2 is of $L_{31}$. The strut pieces 31A and 31B are substantially straight and in a bent situation forming a shape of ">" with a small angle rightwards between the ribs 30-1 and 30-2 via the hinge 36-2, and also the strut pieces 32A and 32B are substantially straight and in a bent situation forming a shape of "<" with a small angle rightwards between the ribs 30-1 and 30-2 via the hinge 36-5. The strut pieces 34A and 34B disposed inside of the substantially U-shaped strut piece 33 is still in a further closed situation forming a small angle.

Figure 5B:
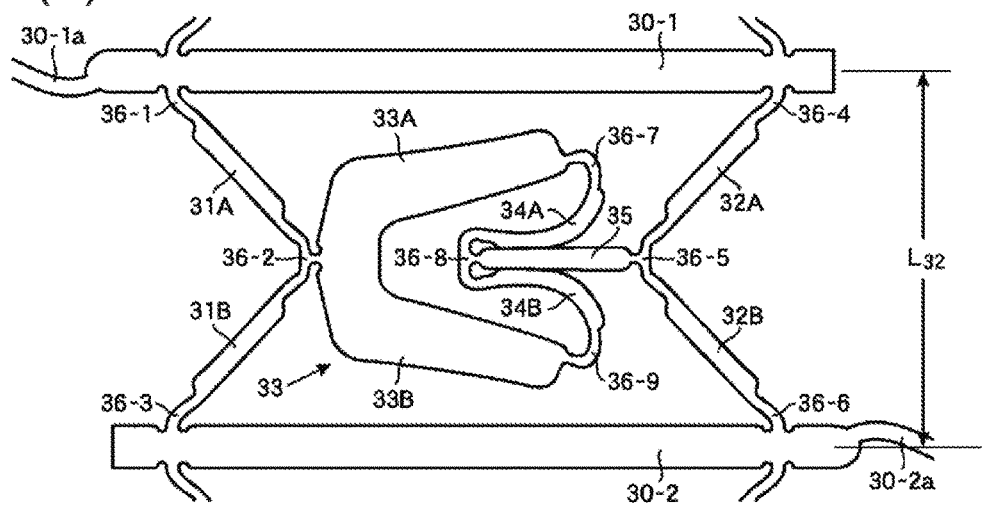

With action of the device expanding its diameter from this state, the distance between the ribs 30-1 and 30-2 is increased to be of $L_{32}$ with diameter of the device expanded to be in a state shown in FIG. 5(b). While angle formed by the strut pieces 31A and 31B is larger at this time, it is smaller than 180° and the strut pieces are in a state before snap-through deformation with a nearly straight shape.

An angle formed by the strut pieces 32A and 32B also becomes larger in a symmetrical manner. As the angle formed by the strut pieces 31A and 31B and the angle formed by the strut pieces 32A and 32B become large, distance between the hinges 36-2 and 36-5 is enlarged, so that the side of the strut pieces 31A and 31B pulls the substantially U-shaped strut piece 33 leftwards via the hinge 36-2 and the side of the strut pieces 32A and 32B pulls, via the strut piece 35 and the hinge 36-8, ends of the strut pieces 34A and 34B connected thereto rightwards.

While the strut pieces 34A and 34B are pulled from their end side connected to the hinge 36-8, they become bent to swell towards the strut piece 35 and, along with this, widen top ends of the branch strut pieces 33A and 33B via the hinges 36-7 and 36-9 upwards-downwards respectively. Due to this, the branch strut pieces 33A and 33B are deformed with the top end sides opened upwards-downwards to some extent as shown in FIG. 5(b).

Figure 5C:
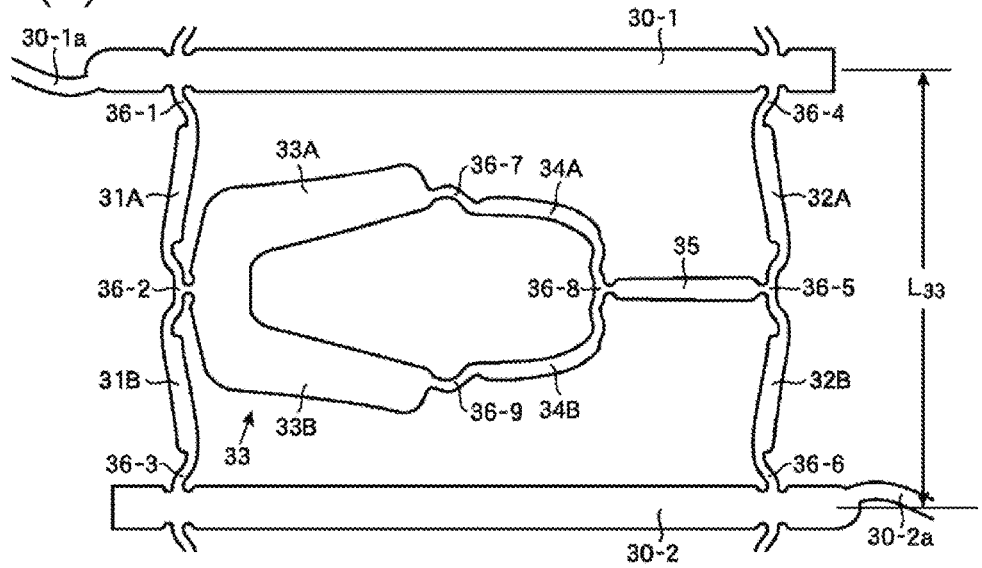

The indwelling medical device expands further its diameter from the state shown in FIG. 5(b) to a state shown in FIG. 5(c) so that the distance between the ribs 30-1 and 30-2 is of $L_{33}$ larger than $L_{32}$. In this process, the strut piece 34A and 34B, with the end sides thereof being pulled further, leave a situation as disposed between the branch strut pieces 33A and 33B of the substantially U-shaped strut piece 33 and are deformed abruptly to be in a state protruding rightwards as shown in FIG. 5(c). This deformation of the strut pieces 34A and 34B as a combination thereof is such that direction of bending is reversed and the strut pieces shift beyond a limit of rising extent of bending between restricted positions of connection to the other stable state at once, thus providing snap-through buckling deformation.

In a process of deformation of the strut pieces 34A and 34B, the distance between a side to the hinge 36-5 of the strut piece 35 and a side to the hinge 36-2 of the substantially U-shaped strut piece 33 is increased at once to press a side to the hinge 36-2 of the strut pieces 31A and 31B a side to the hinge 36-5 of the strut pieces 32A and 32B abruptly leftwards-rightwards, by which the strut pieces 31A and 31B and the strut pieces 32A and 32B are deformed beyond 180° to be a reversed bending state as shown in FIG. 5(c). Such deformation of the strut pieces 31A and 31B and deformation of the strut pieces 32A and 32B are snap-through buckling deformation and the strut pieces 31A and 31B and the state of the strut pieces 32A and 32B shown in FIG. 5(c) are in a stable state with distance between the ribs 30-1 and 30-2 being of $L_{33}$.

In the process of attaining a state shown in FIG. 5(c), the extent of elastic bending deformation is raised in the hinges 36-1, 36-2, and 36-3 connecting the strut pieces 31A and 31B to increase a restoring force and the extent of elastic bending deformation is raised also in the hinges 36-4, 36-5, and 36-6 connecting the strut pieces 32A and 32B to increase the restoring force similarly, which presents a state of providing a high resisting force to further deformation to expand the diameter of the device with bending deformation of the strut pieces providing a force resisting to deformation of elongation.

Consequently, even if the distance between the ribs 30-1 and 30-2 is to be expanded further when a force to expand the diameter of the device is applied, the strut pieces 31A and 31B and the strut pieces 32A and 32B cannot be deformed so as to raise the extent of bending deformation further from a state shown in FIG. 5(c) where the stable state has been attained after snap-through buckling deformation. Further, action by the ribs 30-1 and 30-2 pressing the strut pieces 31A and 31B and the strut pieces 32A and 32B from both sides so as to reduce the distance between the ribs is one preventing the strut pieces 31A and 31B and the strut pieces 32A and 32B having attained the state shown in FIG. 5(c) from returning to the initial state by restoring force.

In such a manner, in a strut having configuration shown in FIG. 5(a) to (c), the strut pieces 31A and 31B and the strut pieces 32A and 32B specifically undergo snap-through buckling deformation. The substantially U-shaped strut piece 33 provided between the strut pieces 31A and 32B and the strut pieces 32A and 32B, the strut pieces 34A and 34B and the strut piece 35 are portions for inducing snap-through buckling deformation in the strut pieces 31A and 31B and the strut pieces 32A and 32B. Further, also the strut 34A and 34B as portions for inducing snap-through buckling deformation in the strut pieces 31A and 31B as well as the strut pieces 32A and 32B undergo snap-through buckling deformation. Thus, such a double bistable structure brings the effect of raising security.

Starting from an initial state shown in FIG. 5(a) such that each strut corresponds to a state where the diameter of the indwelling medical device is reduced, each strut attains a state shown in FIG. 5(b) such that each strut corresponds to a state where the diameter of the device is expanded, and then still further attains a state shown in FIG. 5(c) as the other stable state of bistability of the strut pieces, after which action on the device towards the diameter reduction direction of the device is blocked even if it were applied.

In order to create snap-through buckling deformation in the strut pieces 31A and 31B and the strut pieces 32A and 32B in a process from a state shown in FIG. 5(b) to a state shown in FIG. 5(c), it becomes necessary to decide elements of the configuration of the strut such as the length and the thickness of the substantially U-shaped strut piece 33, the strut pieces 34A and 34B and the strut piece 35 in a positional relationship with the strut pieces 31A and 31B and the strut pieces 32A and 32B so as to enable the strut pieces 34A and 34B to attain, through the state shown in FIG. 5(b), the state shown in FIG. 5(c) having undergone snap-through buckling deformation at once, thus pressing the strut pieces 31A and 31B and the strut pieces 32A and 32B leftwards-rightwards to induce snap-through buckling deformation therein.

The indwelling medical device with each strut in a state shown in FIG. 5(a) is mounted on a balloon catheter in a thin state, which is inserted into a desired luminal organ. Then, the diameter of the indwelling medical device is expanded by expanding the balloon catheter, after which it is caused to indwell within the luminal organ. With this, the indwelling medical device within the luminal organ can secure a function of holding its configuration resisting to pressure from the inner wall of the luminal organ.

In the configuration of the struts forming the elements of the indwelling medical device in luminal organ according to the first to third embodiments explained above, at least one set of two strut pieces is provided that is connected with each other and also to two substantially parallel ribs via hinges in connecting positions on a line substantially perpendicular to the ribs, the two strut pieces are bent forming a small angle between them in a state where the diameter of the indwelling medical device is reduced, the angle between the two strut pieces is enlarged up to nearly 180° when the device comes near to the final step of expanding its diameter, the strut pieces, and the two strut pieces come to have a reversed shape at once with angle between them going beyond 180° through snap-through buckling deformation at a final step of expanding the diameter. The two strut pieces are stable in the state and, even if distance between the two ribs is to be reduced with a force acting to reduce the diameter of the device, the two strut pieces do not return to the initial state, because this action by the ribs is to create deformation in a direction opposite to one in which the two strut pieces are reversed towards the previous state.

While this at least one set of two strut pieces composes main portions holding a state where the indwelling medical device has expanded its diameter, portions acting to induce snap-through buckling deformation in the main portions created in a final step of expanding the diameter of the device are combined with the main portions. Thus, arrangements of the portions inducing snap-through buckling deformation have been specifically exemplified in the embodiments. However, these merely present examples and configuration of portions inducing snap-through buckling deformation in the at least one set of two strut pieces is not limited to these but other configuration of portions may be employed.

Examples have been explained in which a plurality of struts are connected in the circumferential direction of a cylindrical indwelling medical device via ribs in the axial direction of the device with each one rib shared by neighboring struts to form a cylindrical indwelling medical device in each embodiment. However, the ribs are not restricted to those of a straight line in the axial direction, but may be of a bent or curved shape. Further, as long as struts are arranged to be spread in a cylindrical face, ribs are not necessarily indispensable elements, and a plurality of struts may be connected without ribs to form a cylindrical shape. Furthermore, while there may be a case where somewhat plastic deformation is generated in hinges or strut pieces corresponding to material thereof during deformation of an indwelling medical device, such a case may be still favorable as it may provide an effect so as to further increase a force resisting to returning to an initial state.

It has been explained, referring to FIGS. 1(a) and (b), that the cylindrical indwelling medical device having the network structure is composed by connecting a plurality of annular shaped columns of struts by links with each other in due positions in which each strut has both at least one set of strut pieces holding a state of expanded diameter of the device undergoing snap-through buckling deformation and portions for inducing the snap-through buckling deformation and each of the annular shaped columns of struts is formed by connecting a plurality of the struts in the circumferential direction. However, it is not required necessarily that the plurality of annular shaped columns of struts is arranged precisely along circular lines, but it may be that those columns of struts are a little deviated from the circular lines to be in zigzag shape.

Further, in place of configuration in which struts are connected in the circumferential direction to form an annular shape, that is, configuration in which one rotation along the column results in returning to the initial position, the cylindrical indwelling medical device may be composed so as to have a spiral shape of column of struts in which a line of struts composing such column advance by a pitch in the axial direction in a rotation along a cylindrical face and ribs between neighboring struts are connected in due positions via links in the axial direction. This configuration with struts arranged spirally is similar to, for example, one disclosed in Patent Document 1.

The indwelling medical device in luminal organ explained above is composed as a cylindrical body of the polymer or metal material having the network structure in which a plurality of struts are connected in the circumferential direction with a rib shared by neighboring struts, and a plurality of such series of connected struts are connected via links each other in due positions in the axial direction. In order to manufacture such an indwelling medical device, it is necessary to perform processing of a tube-shaped material so as to cause the portions of the struts, ribs and links to remain while removing the other parts. While methods of photolithography employed for processing plane materials is not so adapted for using to perform fine processing to form such configuration of struts, ribs and links, such a configuration can be formed through laser beam machining. Further, finer processing can be made by using a cylindrical reactive ion etching technology as a method developed by the inventor et al. (Journal of Micromechanics and Microengineering, 24 (2014) 055022, pp. 1-8, doi:10.1088/0960-1317/24/5/055022). Furthermore, it is also possible to manufacture such a device by curling up a sheet of film material after it has been processed and connecting both edge faces through adhesion or welding. If a film material is used, methods of photolithography and, of course, laser beam machining can be utilized.

EXPLANATION OF REFERENCE CHARACTERS 1 indwelling medical device
2 rib
2a link
3 strut
10-1, 10-2 rib
10-1a, 10-2a link
10-1b, 10-2b protruding portion
11A, 11B, 11C; 12; 13A, 13B strut piece
14-1, 14-2, 14-3, 14-4, 14-5, 14-6, 14-7, 14-8, 14-9 hinge
20-1, 20-1 rib
20-1a, 20-2a link
20-1b protruding portion
21A, 21B; 22A, 22B; 23 strut piece
24-1, 24-2, 24-3, 24-4, 24-5, 24-6, 24-7 hinge
30-1, 30-2 rib
30-1a, 30-2a link
31A, 31B; 32A, 32B; 33; 34A 34B: 35 strut piece
33A, 33B branch strut piece
36-1, 36-2, 26-3, 36-4, 36-5, 36-6, 36-7, 36-8, 36-9 hinge

What is claimed is:

1. An indwelling medical device for a luminal organ in which a plurality of struts connected with each other are arranged to form a cylindrical shaped body having a network structure as a whole, wherein
    each strut is composed by connecting a plurality of strut pieces integrally via hinges and is deformed to be elongated in a circumferential direction of the indwelling medical device corresponding to expansion of a diameter of the device,
    each strut has at least one set of strut pieces having a bistable structure supporting a load acting to reduce the diameter of the device in a state where the set of strut pieces is deformed from one stable state through snap-through buckling deformation to another stable state in a process of elongation in the circumferential direction and the other strut pieces in the strut are connected so as to provide action to induce snap-through buckling deformation of the at least one set of the strut pieces having the bistable structure in the process of elongation of the strut in the circumferential direction, and
    the load acting to reduce the diameter of the device after snap-through buckling deformation brings action preventing the at least one set of strut pieces having the bistable structure from creating snap-through buckling deformation in a reverse direction, so that an expanded diameter state of the device is held.

2. An indwelling medical device for a luminal organ according to claim 1, wherein
    the at least one set of strut pieces having the bistable structure in each strut are two strut pieces connected via hinges to two neighboring ribs in the circumferential direction so as to be bridged over the two ribs, and a part including the other strut pieces providing action to induce snap-through buckling deformation of the at least one set of the strut pieces is connected to the at least one set of strut pieces having the bistable structure or hinges connected thereto.

3. An indwelling medical device for a luminal organ according to claim 2, wherein
    the struts composing the indwelling medical device are arranged so that each two strut pieces neighboring in the circumferential direction of the indwelling medical device are connected with a rib shared therebetween to form an annular shaped body and a plurality of the annular shaped bodies are connected by connecting the ribs with each other via links in due positions in an axial direction to form the cylindrical indwelling medical device having the network structure, and
    the links have a thickness less than the ribs to be bendable so that the indwelling medical device has flexibility as a whole.

4. An indwelling medical device for a luminal organ according to claim 3, wherein
    in connecting the ribs with each other in due position between an annular shaped body of struts connected in the circumferential direction to another neighboring annular shaped body of struts connected in the circumferential direction, ribs neighboring in the axial direction are connected with each other via links for every more than one ribs in the circumferential direction and ribs disposed between the connected ribs in the circumferential direction are not connected with each other so that flexibility is provided in the indwelling medical device as a whole.

5. An indwelling medical device for a luminal organ according to claim 2, wherein
    the struts composing the indwelling medical device are arranged so that each two strut pieces neighboring in the circumferential direction of the indwelling medical device are connected with a rib shared therebetween to form a series of struts, the series of struts extends along a spiral line to form a cylindrical face and ribs succeeding forwards-backwards in an axial direction by one pitch are connected with each other via links in due positions so as to form the cylindrical indwelling medical device, and
    the links have a thickness less than the ribs to be bendable so that the indwelling medical device has flexibility as a whole.

6. An indwelling medical device in luminal organ according to claim 5, wherein
    in connecting the ribs succeeding forwards-backwards in the axial direction by one pitch with each other via links in due positions to form the cylindrical indwelling medical device with series of struts extending along a spiral line in a cylindrical face, ribs neighboring in the axial direction are connected with each other via links for every more than one ribs in the circumferential direction and ribs disposed between the connected ribs in the circumferential direction are not connected with each other so that flexibility is provided in the indwelling medical device as a whole.

7. An indwelling medical device in luminal organ according claim 2, wherein the part including the other strut pieces providing action to induce the snap-through buckling deformation of the at least one set of the strut pieces having the bistable structure supporting the load acting in a diameter reduction direction of the indwelling medical device has a property of creating snap-through buckling deformation by itself along with inducing snap-through buckling deformation of the at least one set of two strut pieces having the bistable structure when the indwelling medical device expands in diameter, so that each strut provides a double bistable structure.

* * * * *